United States Patent
Kitazawa et al.

(10) Patent No.: US 6,310,086 B1
(45) Date of Patent: Oct. 30, 2001

(54) INDOLE DERIVATIVES AND MEDICINAL COMPOSITIONS CONTAINING THE SAME

(75) Inventors: Makio Kitazawa, Matsumoto; Toshiaki Yamaguchi, Oaza; Hiroshi Miyata, Matsumoto; Yukiyoshi Ajisawa, Okaya, all of (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/622,871

(22) PCT Filed: Feb. 19, 1999

(86) PCT No.: PCT/JP99/00732

§ 371 Date: Oct. 23, 2000

§ 102(e) Date: Oct. 23, 2000

(87) PCT Pub. No.: WO99/43652

PCT Pub. Date: Sep. 2, 1999

(30) Foreign Application Priority Data

Feb. 27, 1998 (JP) .................................. 10-090572

(51) Int. Cl.$^7$ ........................ A61K 31/404; C07D 209/08
(52) U.S. Cl. ................................... 514/415; 548/503
(58) Field of Search ............................. 548/503; 514/415

(56) References Cited

U.S. PATENT DOCUMENTS

| | | | |
|---|---|---|---|
| 5,021,410 | 6/1991 | Burke | 514/213 |
| 5,387,603 | 2/1995 | Kitazawa et al. | 514/415 |

FOREIGN PATENT DOCUMENTS

| | | |
|---|---|---|
| 7-330725 | 12/1995 | (JP) . |
| 7-330726 | 12/1995 | (JP) . |
| 8-143557 | 6/1996 | (JP) . |
| 9-12563 | 1/1997 | (JP) . |
| WO 99/15202 * | 4/1999 | (WO) . |
| 9943652 | 9/1999 | (WO) . |

OTHER PUBLICATIONS

"KMD–3213, A Novel $\alpha_{1A}$—Adrenoceptor Antagonist, Potently Inhibits the Functional $\alpha_1$—Adrenoceptor in Human Prostate" by Moriyama, et. al., European Journal of Pharmacology, vol. 337 (1997), pp. 39–42.

"Effect of KMD–3213, An $\alpha_{1A}$—Adrenoceptor—selective antagonist, on the Contractions of Rabbit Prostate and Rabbit and Rat Aorta" by Yamagishi, et.al, European Journal of Pharmacology, vol. 315 (1996) pp. 73–79.

"KMD–3213, A Novel, Potent, $\alpha_{1A}$—Adrenoceptor—Selective Antagonist: Characterization Using Recombinant Human $\alpha_1$—Adrenoceptors and Native Tissues" by Shibata, et. al., Molecular Pharmacology, 48:250–258 (1995).

* cited by examiner

Primary Examiner—Fiona T. Powers
(74) Attorney, Agent, or Firm—Stuart D. Frenkel; Liniak, Berenato, Longacre & White

(57) ABSTRACT

The present invention relates to indole derivatives represented by the general formula:

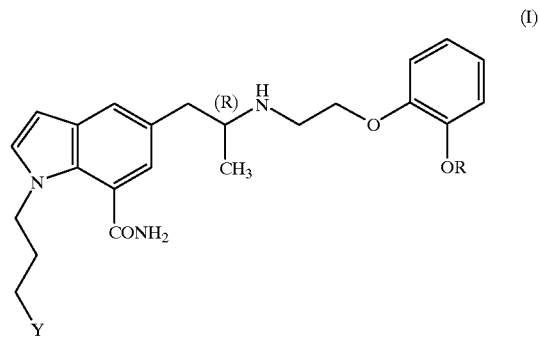

(I)

(wherein R represents an ethyl group or a 2,2,2-trifluoroethyl group; Y represents a hydroxy group or a pivaloyloxy group; and the carbon atom marked with (R) represents a carbon atom in (R) configuration) and pharmaceutically acceptable salts thereof, which have potent and prolonged reducing effects on intraocular pressure and are useful as agents for lowering intraocular pressure.

13 Claims, No Drawings

INDOLE DERIVATIVES AND MEDICINAL COMPOSITIONS CONTAINING THE SAME

TECHNICAL FIELD

The present invention relates to novel indole derivatives and pharmaceutically acceptable salts thereof which are useful as medicaments.

BACKGROUND ART

Up to this time, Timolol maleate and Isopropyl unoprostone are known as example of compounds that have been used as agents for lowering intraocular pressure.

Recently, Bunazosin hydrochloride, which has $\alpha_1$-adrenoceptor blocking effect a mechanism (hereinafter referred to as $\alpha_1$-blocking effect) quite different from the actions of Timolol maleate and Isopropyl Unoprostone, has been developed as an agent for the treatment of glaucoma and is attracting public attention. However, Bunazosin hydrochloride was primarily developed as an agent for the treatment of hypertension. Therefore, Bunazosin hydrochloride has potent action on the blood pressure and it is wondered that it might induce side effects such as hypotension and orthostatic hypotension.

Generally, most agents for lowering intraocular pressure are topically applied as eyedrops. Even in this case an active component distributes to all over the body via the blood flow and it is expected that it shows systemic action. Therefore, it is desired that expected systemic side effects are minimized even in topical administration.

Compounds which are absorbed into eyes immediately after the application and act for a long period are most preferable so as to act topically as much as possible.

Consequently, compounds which have potent reducing effect on intraocular pressure with less incidence of side effects such as hypotension and orthostatic hypotension, are rapidly absorbed into eyes after the installation and act for a long period are mostly recommended as agents for lowering intraocular pressure.

DISCLOSURE OF THE INVENTION

The present invention relates to an indole derivative represented by the general formula:

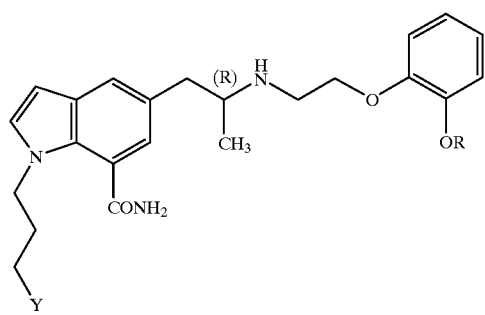

(wherein R represents an ethyl group or a 2,2,2-trifluoroethyl group; Y represents a hydroxy group or a pivaloyloxy group with the proviso that Y represents a pivaloyloxy group when R represents a 2,2,2-trifluoroethyl group; and the carbon atom marked with (R) represents a carbon atom in (R) configuration) or a pharmaceutically acceptable salts thereof.

The present invention relates to a pharmaceutical composition comprising an indole derivative represented by the general formula:

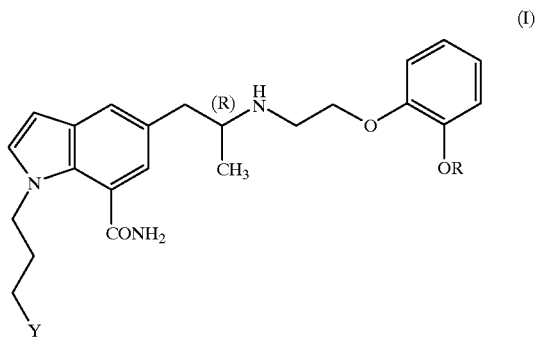

(wherein R represents an ethyl group or a 2,2,2-trifluoroethyl group; Y represents a hydroxy group or a pivaloyloxy group with the proviso that Y represents a pivaloyloxy group when R represents a 2,2,2-trifluoroethyl group; and the carbon atom marked with (R) represents a carbon atom in (R) configuration) or a pharmaceutically acceptable salt thereof.

The present invention relates to an agent for lowering intraocular pressure which comprises as the active ingredient an indole derivative represented by the general formula:

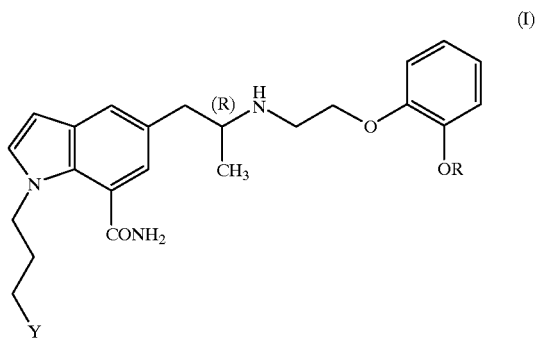

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

The present invention relates to an agent for the prevention or treatment of glaucoma or ocular hypertension which comprises as the active ingredient an indole derivative represented by the general formula:

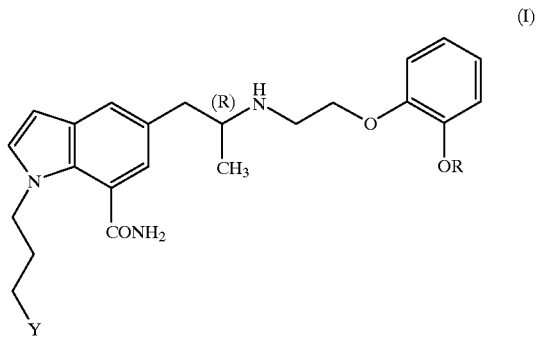

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

The present invention relates to a method for the prevention or treatment of glaucoma or ocular hypertension which comprises administrating a therapeutically effective amount of an indole derivative represented by the general formula:

(I)

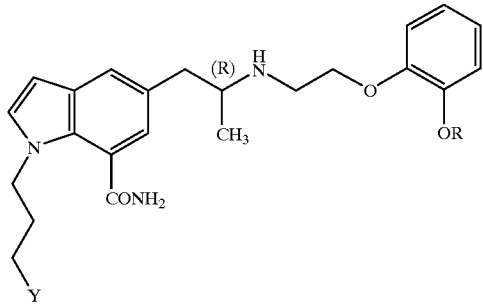

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

The present invention relates to a use of an indole derivative represented by the general formula:

(I)

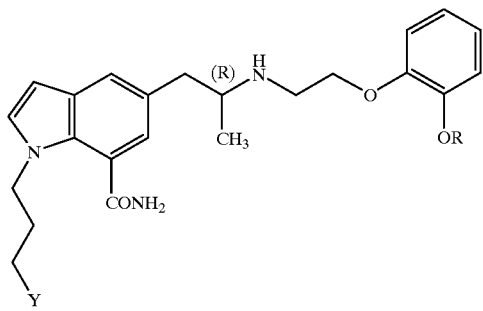

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof for the manufacture of a pharmaceutical composition for the prevention or treatment of glaucoma or ocular hypertension.

The present invention relates to a use of an indole derivative represented by the general formula:

(I)

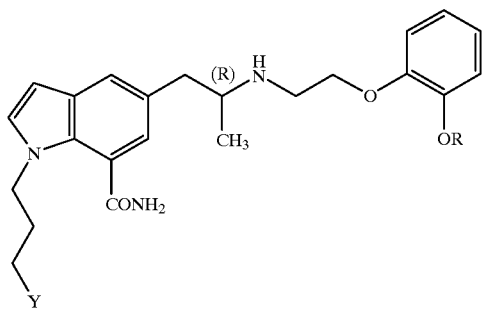

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof as an agent for the prevention or treatment of glaucoma or ocular hypertension.

Furthermore, the present invention relates a process for the manufacture of a pharmaceutical composition for the prevention or treatment of glaucoma or ocular hypertension, characterized in the use, as an essential constituent of said pharmaceutical composition, of an indole derivative represented by the general formula:

(I)

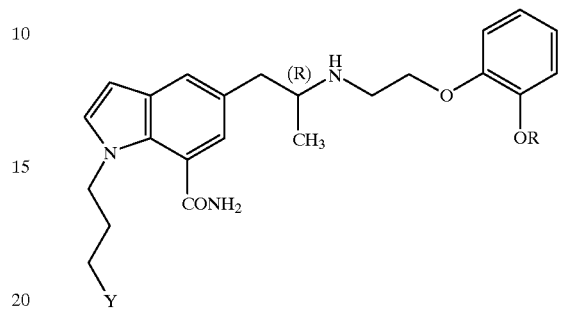

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

BEST MODE FOR CARRYING OUT THE INVENTION

The present inventors have studied in order to find drugs which have potent and prolonged $\alpha_1$-blocking effect with less side effects such as hypotension and orthostatic hypotension and with high permeability into eyes. As a result, it has been found that (R)-1-(3-hydroxypropyl)-5-[2-[[2-[2-(2,2,2-trifluoroethoxy)phenoxy]ethyl]amino]propyl]-1H-indole-7-carboxamide (hereinafter referred to as Compound A), one of indole derivatives which were previously developed as agents for the treatment of dysuria having selective suppressive effect on urethral contractions with less affecting the blood pressure (published Japanese patent application (Kokai) No. Hei 7-330726), and (R)-5-[2-[[2-(2-ethoxyphenoxy)ethyl]-amino]propyl]-1-(3-hydroxypropyl)-1H-indole-7-carboxamide (hereinafter referred to as Compound B) hydrochloride have extremely potent $\alpha_1$-blocking effect, more than 70-fold stronger than Bunazosin hydrochloride, with less incidence of side effects such as hypotension and orthostatic hypotension and that these compounds are expected to act for a long period because of low excretion rate after the permeation into eyes and are useful as preferred agents for lowering intraocular pressure.

Furthermore, because Compounds A and B have poor permeability of membranes such as cornea, the present inventors have studied in order to find derivatives which have high membrane permeability and rapidly convert into the poorly membrane permeable Compound A or B after the permeation. As a result, it has been found surprisingly that pivalic acid ester derivatives represented by the general formula:

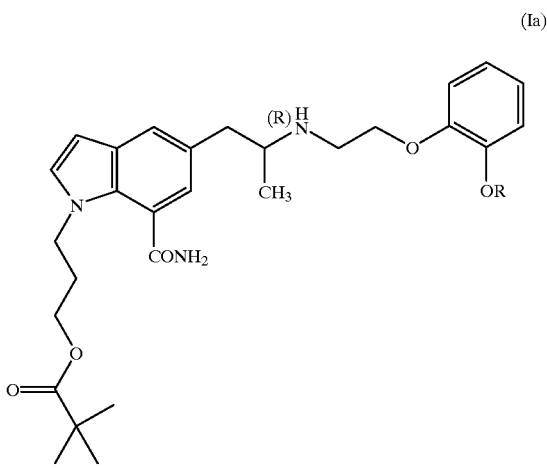

(wherein R represents an ethyl group or a 2,2,2-trifluoroethyl group; and the carbon atom marked with (R) represents a carbon atom in (R) configuration) have extremely high membrane permeability, are rapidly converted into Compound A or B having poor membrane permeability by hydrolase after the permeation and are extremely stable in aqueous solution which is normal form of eyedrops, thereby forming the basis of the present invention.

Namely, the present inventors have found that Compounds A and B have potent $\alpha_1$-blocking effect and are preferred compounds as agents for lowering intraocular pressure. However, these compounds have poor corneal permeability and their concentration in aqueous humor is fairly low when these compounds are topically applied as eyedrops. Therefore, the present inventors have extensively studied in order to find the way to obtain fully drug concentration in aqueous humor even when applying as eyedrops.

In order to find derivatives of Compound A or B which are easily converted into Compound A or B respectively in the event of the permeation of cornea or in aqueous humor and are able to show their effects rapidly, the present inventors have converted Compound A or B into various derivatives and assessed their facility of cleavage by endogenous hydrolase by measuring ratio of conversion into Compound A or B in the blood with the time course. As a result, for example, it has been found surprisingly that ratios of conversion of some ester derivatives of Compound A into Compound A after 30 minutes in the blood were extremely low, about 12% in the case of the corresponding 2-ethylbutyrate derivative, about 4% in the case of the corresponding 2,2-dimethylvalerate derivative, about 2% in the case of the corresponding α,α-dimethylphenyl acetate derivative and about 6% in the case of the corresponding 2,2-dimethyl butyrate derivative, respectively. While the corresponding pivalate derivative was already converted into Compound A in the ratio of about 67% after 30 minutes and almost Compound A after 2 hours. Thus, the present inventors have found that the pivalate derivatives represented by the above general formula (Ia) of the present invention are different from other carboxylate derivatives and are specific compounds which are very easily converted into Compound A or B by endogenous hydrolase in cornea or aqueous humor.

Then, the present inventors have measured drug concentration in aqueous humor after installation on rabbit eyes with the time course in order to confirm corneal permeability of this pivalate derivative. For example, in the case of installation on eyes of pivalate derivative hydrochloride of Compound B, drug concentration of Compound B in aqueous humor was about 70 times higher after 20 minutes and about 27 times higher after 2 hours than that in the case of the installation of Compound B hydrochloride. Thus, the pivalate derivatives represented by the above general formula (Ia) of the present invention are extremely excellent compounds in corneal permeability and long-acting compounds.

In addition, in the above experiment, pivalate derivative of Compound B was rapidly converted into Compound B in the event of the permeation of cornea or in aqueous humor and could not be detected in aqueous humor at all even after 20 minutes. Accordingly, the pivalate derivatives represented by the above general formula (Ia) of the present invention are permeable rapidly and favorably through corneal and have property to be converted into Compound A or B rapidly. Therefore, these are extremely preferred compounds to reveal the effect of Compound A or B surely and rapidly. In fact, in an experiment using rabbits, it was confirmed that the pivalate derivatives represented by the above general formula (Ia) show very potent and prolonged reducing effect on intraocular pressure. Accordingly, the pivalate derivatives represented by the above general formula (Ia) are extremely useful compounds as eyedrops for the prevention or treatment of glaucoma or ocular hypertension.

Furthermore, the pivalate derivatives represented by the above general formula (Ia) of the present invention are hardly decomposed in the state of eyedrops under high temperature and are extremely stable compounds. For example, when pivalate derivative of Compound A was allowed to stand for about 1 month at 40° C. in the state of aqueous solution, only about 0.1% of this compound was decomposed into Compound A. Similarly, about 1.1% of this compound was decomposed into Compound A even at 70° C. Thus, the pivalate derivatives represented by the above general formula (Ia) of the present invention are extremely stable compounds in the state of aqueous solution and eyedrops containing the said compounds are excellent in long storage stability. Therefore, the pivalate derivatives represented by the above general formula (Ia) of the present invention are highly suitable compounds to topical application as eyedrops.

The compounds represented by the above general formula (I) of the present invention, for example, can be prepared by protecting the secondary nitrogen atom of an indoline derivative represented by the general formula:

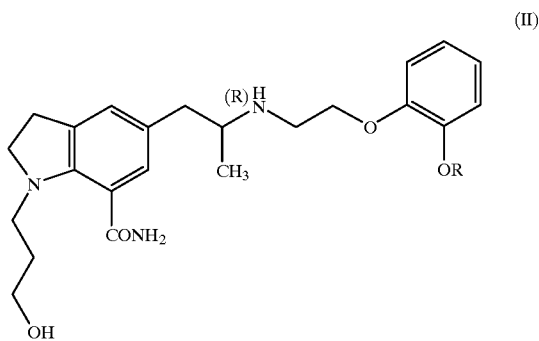

(wherein R and the carbon atom marked with (R) have the same meanings as defined above) with a protecting group such as a tert-butoxycarbonyl group in the usual way, allowing to oxidize the indoline ring of the resulting compound in the presence of a metal catalyst such as palladium carbon and ammonium formate to prepare an indole derivative represented by the general formula:

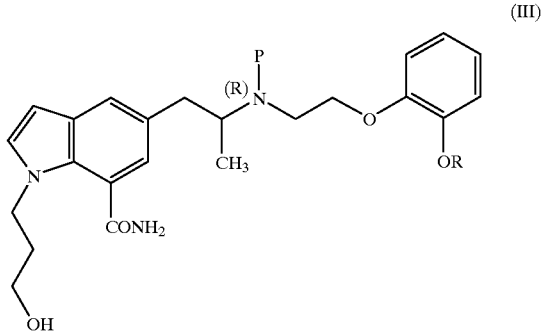

(III)

(wherein P represents an amino-protective group; and R and the carbon atom marked with (R) have the same meanings as defined above), allowing to react with a pivaloyl halide in the presence of a base as occasion demands and removing the protective group in the usual way.

Of the compounds represented by the above general formula (I) of the present invention, the pivalate derivatives represented by the above general formula (Ia) can be also prepared by protecting the secondary nitrogen atom of an indoline derivative represented by the above general formula (II) with a protecting group such as a tert-butoxycarbonyl group in the usual way, allowing the resulting compound to react with a pivaloyl halide in the presence of a base to prepare an indoline derivative represented by the general formula:

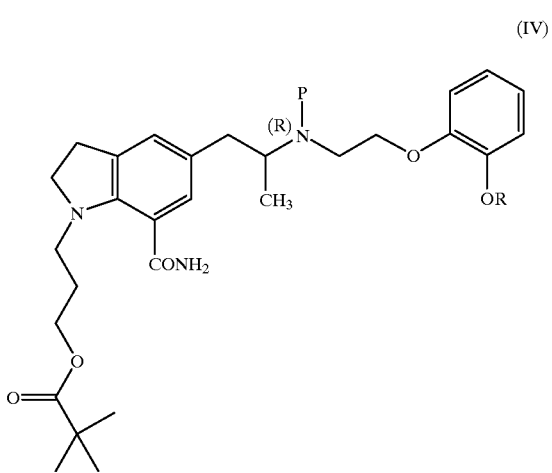

(IV)

(wherein P, R and the carbon atom marked with (R) have the same meanings as defined above), allowing to oxidize the indoline ring of the resulting compound in the presence of a metal catalyst such as palladium carbon and ammonium formate, and removing the protective group in the usual way.

The indole derivatives represented by the above general formula (I) of the present invention can be converted into their pharmaceutically acceptable salts in the usual way. Examples of such salts include acid addition salts with mineral acids (e.g., hydrochloric acid, hydrobromic acid, hydroiodic acid, sulfuric acid, nitric acid, phosphoric acid and the like) and acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, salicylic acid, benzoic acid, adipic acid, carbonic acid, glutamic acid, aspartic acid and the like).

When the indole derivatives represented by the above general formula (I) of the present invention and pharmaceutically acceptable salts thereof are employed in the practical treatment, various administration forms are applicable. Among the forms, topical administration using eyedrops and the like is preferred. Eyedrops can be suitably formulated in accordance with conventional methods. For example, eyedrops can be prepared by adding the pivalate derivatives represented by the above general formula (Ia) of the present invention to sterile purified water, dissolving by adding suitably pharmaceutical additives such as antiseptics, isotonicities and buffers, if necessary, under warming and filtering to remove dusts and/or microbes.

The dosage is appropriately decided depending on the sex, age, body weight, degree of symptoms and the like of each patient to be treated. For example, installation on eyes of solution ranging from 0.001 to 0.5% 1 to 3 times per day is preferred in the case of eyedrops.

EXAMPLES

The present invention is further illustrated in more detail by way of the following Reference Examples, Examples and Test Examples. The present invention is not limited thereto.

Reference Example 1

(R)-3-[7-Cyano-5-[2-[[2-(2-ethoxyphenoxy)ethyl] amino]-propyl]-2,3-dihydro-1H-indol-1-yl]propyl Benzoate To a solution of potassium carbonate (32.3 g) in distilled water(120 ml) was added ethyl acetate (120 ml), and (R)-3-[5-(2-aminopropyl)-7-cyano-2,3-dihydro-1H-indol-1-yl] propyl benzoate L-tartrate (12.0 g) was added portionwise to the mixture with stirring. After reaction for 1 hour, the reaction mixture was extracted with ethyl acetate, and the ethyl acetate layer was washed with 10% aqueous potassium carbonate solution and brine subsequently, and dried over anhydrous sodium sulfate. The solvent was removed in vacuo to give (R)-3-[5-(2-aminopropyl)-7-cyano-2,3-dihydro-1H-indol-1-yl]propyl benzoate (8.98 g) as a brown oil.

The resulting (R)-3-[5-(2-aminopropyl)-7-cyano-2,3-dihydro-1H-indol-1-yl]propyl benzoate (8.98 g) was dissolved in tert-butanol (43 ml). 2-(2-Ethoxyphenoxy) ethyl methanesulfonate (7.02 g) and sodium carbonate (2.86 g) were added to the solution, and the mixture was heated under ref lux overnight. The reaction mixture was concentrated in vacuo, a saturated aqueous sodium bicarbonate solution was added to the residue and the mixture was extracted with ethyl acetate. The ethyl acetate layer was washed with a saturated aqueous sodium bicarbonate solution and brine subsequently and dried over anhydrous sodium sulfate. The solvent was removed in vacuo, the residue was purified by column chromatography on silica gel (eluent: ethyl acetate and ethyl acetate/methanol=100/6). Azeotropic concentration of the resulting oily material gave (R)-3-[7-cyano-5-[2-[[2-(2-ethoxyphenoxy)ethyl]amino]-propyl]- 2,3-dihydro-1H-indol-1-yl]propyl benzoate (7.46 g) as a brown oil.

$^1$H-NMR (CDCl$_3$) δ ppm: 1.04 (d, J=6.0 Hz, 3H), 1.41 (t, J=6.9 Hz, 3H), 2.10–2.20 (m, 2H), 2.42 (dd, J=13.6, 6.9 Hz, 1H), 2.63 (dd, J=13.6, 6.0 Hz, 1H), 2.80–3.10 (m, 5H), 3.50–3.60 (m, 2H), 3.75 (t, J=7.3 Hz, 2H), 4.00–4.15 (m, 4H), 4.40–4.50 (m, 2H), 6.85–7.00 (m, 6H), 7.40–7.50 (m, 2H), 7.50–7.60 (m, 1H), 8.00–8.10 (m, 2H); Specific Rotation: $[\alpha]_D^{27}$=−14.8° (c=1.04, Methanol).

Reference Example 2

(R)-5-[[2-2-(2-Ethoxyphenoxy)ethyl]amino]propyl-1-(3-hydroxypropyl)-2,3-dihydro-1H-indole-7-carbonitrile (R)-3-[7-Cyano-5-[2-[[2-(2-ethoxyphenoxy)ethyl]-amino]propyl]-2,3-dihydro-1H-indol-1-yl]propyl benzoate (7.23 g) was dissolved in methanol (46 ml) and the solution was added to a solution of potassium hydroxide (1.54 g) in distilled water (9.2 ml). After being heated under reflux for 1 hour, the reaction mixture was concentrated in vacuo. Distilled water (100 ml) was added to the residue and the resulting mixture was extracted with ethyl acetate. The ethyl acetate layer was washed with a saturated aqueous sodium bicarbonate solution and brine, and dried over anhydrous sodium sulfate. The solvent was removed in vacuo, and the residue was dissolved in toluene(30 ml) and the toluene was removed in vacuo to give (R)-5-[2-[[2-(2-ethoxyphenoxy) ethyl]amino]propyl]-1-( 3-hydroxypropyl)-2,3-dihydro-1H-indole-7-carbonitrile(6.06 g) as a pale brown oil.

$^1$H-NMR (CDCl$_3$) δ ppm: 1.05 (d, J=6.0 Hz, 3H), 1.41 (t, J=6.9 Hz, 3H), 1.50–1.90 (m, 1H), 1.85–2.00 (m, 2H), 2.43 (dd, J=13.6, 6.9 Hz, 1H), 2.63 (dd, J=13.6, 6.3 Hz, 1H), 2.80–3.10 (m, 5H), 3.50–3.60 (m, 2H), 3.67 (t, J=7.3 Hz, 2H), 3.75–3.85 (m, 2H), 4.00–4.15 (m, 4H), 6.85–7.30 (m, 6H); Specific Rotation: $[\alpha]_D^{27}$=−19.4° (c=1.06, Methanol).

Reference Example 3

(R)-5-[2- [[2-(2-Ethoxyphenoxy)ethyl]amino] propyl]-1-(3-hydroxypropyl)-2,3-dihydro-1H-indole-7-carboxamide (R)-5-[2-[[2-(2-Ethoxyphenoxy)ethyl]amino]propyl]-1-(3-hydroxypropyl)-2,3-dihydro-1H-indole-7-carbonitrile (5.95 g) was dissolved in dimethylsulfoxide (16.4 ml), and 5N sodium hydroxide solution (0.25 ml) was added to the solution. To the mixture was added 30% hydrogen peroxide (1.55 ml) keeping inner temperature below 25° C., and the mixture was stirred overnight at an inner temperature of 25–30° C. A solution of sodium sulfite (2.39 g) in distilled water (82 ml) was added to the reaction mixture, and the mixture was extracted with ethyl acetate. The ethyl acetate layer was washed with a saturated aqueous sodium bicarbonate solution, distilled water and brine subsequently, and dried over anhydrous sodium sulfate. The solvent was removed in vacuo, the residue was recrystallized from ethyl acetate to give (R)-5-[2-[[2-(2-ethoxyphenoxy)-ethyl]amino]propyl]-1-(3-hydroxypropyl)-2,3-dihydro-1H-indole-7-carboxamide (4.72 g).

$^1$H-NMR (CDCl$_3$) δ ppm: 1.07 (d, J=6.2 Hz, 3H), 1.37 (t, J=7.0 Hz, 3H), 1.60–1.85 (m, 3H), 2.54 (dd, J=13.6, 6.5 Hz, 1H), 2.68 (dd, J=13.6, 6.4 Hz, 1H), 2.85–3.10 (m, 6H), 3.19 (t, J=6.6 Hz, 2H), 3.35–3.45 (m, 2H), 3.75 (t, J=5.4 Hz, 2H), 3.95–4.20 (m, 4H), 5.70 (br s, 1H), 6.66 (br s, 1H), 6.80–6.95 (m, 4H), 7.02 (s, 1H), 7.16 (s, 1H); Specific Rotation: $[\alpha]_D^{27}$=−15.3° (c=0.98, Methanol).

Reference Example 4

Tert-Butyl (R)-N-[2-[7-carbamoyl-1-(3-hydroxypropyl)-2,3-dihydro-1H-indol-5-yl]-1-methylethyl]-N-[2-(2-ethoxy-phenoxy)ethyl] carbamate (R)-5-[2-[[2-(2-Ethoxyphenoxy)ethyl]amino]propyl]-1-(3-hydroxypropyl)-2,3-dihydro-1H-indole-7-carboxamide (10.9 g) was dissolved in methylene chloride(100 ml), and a solution of di-tert-butyl dicarbonate (5.87 g) in methylene chloride (25 ml) was added dropwise to the solution with stirring under ice-cooling. After being stirred for 30 minutes under the same condition, the reaction mixture was stirred for 10 hours at room temperature. The reaction mixture was concentrated in vacuo, and the residue was dissolved in ethyl acetate (150 ml). The solution was washed with 10% aqueous citric acid solution, a saturated aqueous sodium bicarbonate solution and brine subsequently, and dried over anhydrous sodium sulfate. The solvent was removed in vacuo to give pale brown amorphous tert-butyl (R)-N-[2-[7-carbamoyl-1-(3-hydroxypropyl)-2,3-dihydro-1H-indol-5-yl]-1-methylethyl]-N-[2-(2-ethoxyphenoxy)ethyl] carbamate (10.2 g).

$^1$H-NMR (CDCl$_3$) δ ppm: 1.20–1.50 (m, 15H), 1.70–1.85 (m, 2H) 2.50–4.40 (m, 18H), 5.75 (br h, 1H), 6.63 (br s, 1H), 6.80–7.20 (m, 6H); Specific Rotation: $[\alpha]_D^{27}$=−50.4° (c=1.27, Methanol).

Example 1

(R)-5-[2-[[2-(2-Ethoxyphenoxy)ethyl]amino] propyl]-1-(3-hydroxypropyl)-1H-indole-7-carboxamide (Compound B)

tert-Butyl (R)-N-[2-[7-carbamoyl-1-(3-hydroxy-propyl)-2,3-dihydro-1H-indol-5-yl]-1-methylethyl]-N-[2-(2-ethoxyphenoxy)ethyl]carbamate (4.93 g) was dissolved in methanol (150 ml), and 10% palladium on carbon (490 mg) and ammonium formate (2.96 g) were added to the solution. After the mixture was heated under reflux for 36 hours and cooled, the insoluble material was filtered off. The solvent was removed in vacuo, and the residue was dissolved in methanol (150 ml). 10% Palladium on carbon (490 mg) and ammonium formate (2.96 g) were added to the solution. After the mixture was heated under reflux for 24 hours and cooled, the insoluble material was filtered off. The filtrate was concentrated in vacuo, and the residue was dissolved in ethyl acetate. The solution was washed with water and brine, and dried over anhydrous sodium sulfate. The solvent was removed in vacuo to give white amorphous tert-butyl (R)-N-[2-[7-carbamoyl-1-(3-hydroxypropyl)-1H-indol-5-yl]-1-methylethyl]-N-[2-(2-ethoxyphenoxy)ethyl]-carbamate (4.55 g).

$^1$H-NMR (CDCl$_3$) δ ppm: 1.05–1.50 (m, 15H), 1.90–2.10 (m, 2H) 2.70–3.00 (m, 3H), 3.30–3.75 (m, 4H), 3.80–4.65 (m, 7H), 5.75–5.95 (m, 1H), 6.40–6.65 (m, 2H), 6.75–7.55 (m, 7H); Specific Rotation: $[\alpha]_D^{30}$=−47.° (c=1.05, Methanol).

tert-Butyl (R)-N-[2-[7-carbamoyl-1-(3-hydroxy-propyl)-1H-indol-5-yl]-1-methylethyl]-N-[2-(2-ethoxyphenoxy) ethyl]carbamate (4.45 g) was dissolved in isopropanol (50 ml), and concentrated hydrochloric acid (25 ml) was added portionwise to the solution under ice-cooling with stirring. After the mixture was stirred for 3 hours at room temperature, a saturated aqueous sodium bicarbonate solution was added to the reaction mixture under ice-cooling and the mixture was extracted with ethyl acetate. The ethyl acetate layer was washed with brine, and dried over anhydrous sodium sulfate. The solvent was removed in vacuo, and the residue was purified by column chromatography on aminopropyl silica gel (eluent: methylene chloride/methanol=20/1) to give white amorphous (R)-5-[2-[[2-(2-ethoxyphenoxy)ethyl]amino]-propyl]-1-(3-hydroxypropyl)-1H-indole-7-carboxamide (1.27 g). Unpurified mixture was further purified by column chromatography on aminopropyl silica gel (eluent:ethyl acetate/ethanol=7/1) and the purified product was combined with the previously purified product to give white amorphous (R)-5-[2-[[2-(2-ethoxyphenoxy) ethyl]amino]propyl]-1-(3-hydroxypropyl)-1H-indole-7-carboxamide (2.39 g).

$^1$H-NMR (CDCl$_3$) δ ppm: 1.11 (d, J=6.3 Hz, 3H), 1.25 (t, J=7.0 Hz, 3H), 1.95–2.10 (m, 2H), 2.70–3.20 (m, 6H), 3.52 (t, J=5.6 Hz, 2H), 3.93 (q, J=7.0 Hz, 2H), 4.00–4.20 (m, 2H), 4.38 (t, J=7.0 Hz, 2H), 5.90 (br s, 1H), 6.38 (br s, 1H), 6.49 (d, J=3.2 Hz, 1H), 6.75–6.95 (m, 4H), 7.11 (d, J=3.2 Hz, 1H), 7.19 (d, J=1.5 Hz, 1H), 7.53 (d, J=1.4 Hz, 1H); Specific Rotation: $[α]_D^{30}$=−15.5° (c=1.02, Methanol).

Example 2

(R)-5-[2-[[2-(2-Ethoxyphenoxy) ethyl]amino] propyl]-1-(3-hydroxypropyl)-1H-indole-7-carboxamide Hydrochloride (Compound B Hydrochloride)

(R)-5-[2-[[2-(2-Ethoxyphenoxy)ethyl]amino]propyl]-1-(3-hydroxypropyl)-1H-indole-7-carboxamide (862 μg) was dissolved in ethanol (5 ml), and 2N hydrochloric acid(985 μl) was added to the solution. The solvent was removed in vacuo, the residue was dissolved in ethanol (3 ml), and ethyl acetate (12 ml) was added to the solution. After the mixture was allowed to stand, the resulting crystals were collected by filtration to give (R)-5-[2-[[2-(2-ethoxyphenoxy)ethyl] amino]propyl]-1-(3-hydroxypropyl)-1H-indole-7-carboxamide hydrochloride (821 mg).

$^1$H-NMR (DMSO-d$_6$) δ ppm: 1.19 (d, J=6.4 Hz, 3H), 1.26 (t, J=7.0 Hz, 3H), 1.70–1.85 (m, 2H), 2.65–2.80 (m, 1H), 3.20–3.55 (m, 5H), 3.64 (br s, 1H), 4.02 (q, J=7.0 Hz, 2H), 4.20–4.40 (m, 4H), 4.55 (t, J=5.0 Hz, 1H), 6.45 (d, J=3.1 Hz, 1H), 6.85–7.15 (m, 5H), 7.36 (d, J=3.1 Hz, 1H), 7.49 (d, J=1.3 Hz, 1H), 7.60 (br s, 1H) 7.99 (br s, 1H), 9.05–9.30 (m, 2H); Specific Rotation: $[α]_D^{30}$=−7.8° (c=1.16, Methanol).

Example 3

(R)-3-[7-Carbamoyl-5-[2-[[2-(2-ethoxyphenoxy) ethyl]amino]-propyl]-1H-indol-1-yl]propyl Pivalate (Compound C)

tert-Butyl (R)-N-[2-[7-carbamoyl-1-(3-hydroxy-propyl)-2,3-dihydro-1H-indol-5-yl]-1-methylethyl]-N-[2-(2-ethoxyphenoxy)ethyl]carbamate (6.24 g) was dissolved in dry pyridine (9.4 ml), and pivaloyl chloride (1.54 ml) was added to the solution. The mixture was stirred overnight at room temperature, and a saturated aqueous sodium bicarbonate solution was added to the reaction mixture. The mixture was extracted with ethyl acetate, and the ethyl acetate layer was washed with a saturated aqueous sodium bicarbonate solution and brine, and dried over anhydrous sodium sulfate. The solvent was removed in vacuo, and the residue was purified by column chromatography on aminopropyl silica gel (eluent:hexane/ethyl acetate=1/1) to give colorless amorphous (R)-3-[5-[2-[N-(tert-butoxycarbonyl)-N-[2-(2-ethoxyphenoxy)ethyl]amino]-propyl]-7-carbamoyl-2,3-dihydro-1H-indol-1-yl]propyl pivalate (4.30 g).

$_1$H-NMR (CDCl$_3$) δ ppm: 1.15–1.50 (m, 24H), 1.85–2.00 (m, 2H) 2.55–3.20 (m, 6H), 3.30–3.60 (m, 4H), 3.85–4.40 (m, 7H), 5.52 (br s, 1H), 6.80–7.40 (m, 7H); Specific Rotation: $[α]_D^{27}$=−38.3° (c=1.03, Methanol).

(R)-3-[5-[2-[N-(tert-Butoxycarbonyl)-N-[2- (2-ethoxyphenoxy)ethyl]amino]propyl]-7-carbamoyl-2,3-dihydro-1H-indol-1-yl]propyl pivalate (8.53 g) was dissolved in methanol (280 ml), and 10% palladium on carbon (853 mg) and ammonium formate (3.97 g) were added to the solution. The mixture was heated under reflux for 13 hours, and the catalysts were filtered off. The solvent was removed in vacuo to give pale green amorphous (R)-3-[5-[2-[N-(tert-butoxycarbonyl)-N-[2-(2-ethoxyphenoxy)ethyl]amino] propyl]-7-carbamoyl-1H-indol-1-yl]propyl pivalate (8.20 g).

$^1$H-NMR (CDCl$_3$) δ ppm: 1.05–1.50 (m, 24H), 1.90–2.10 (m, 2H) 2.70–3.05 (m, 2H), 3.30–3.75 (m, 2H), 3.85–4.70 (m, 9H), 5.66 (br s, 1H), 6.35–6.50 (m, 2H), 6.75–7.55 (m, 7H); Specific Rotation: $[α]_D^{27}$=−44.5° (c=1.06, Methanol).

(R)-3-[5-[2-[N-(tert-Butoxycarbonyl)-N-[2-(2-ethoxy-phenoxy)ethyl]amino]propyl]-7-carbamoyl-1H-indol-1-yl] propyl pivalate (7.81 g) was dissolved in isopropanol (78 ml), and concentrated hydrochloric acid (39 ml) was added dropwise over a period of 10 minutes to the solution under ice-cooling with stirring. After the mixture was stirred for 4 hours at room temperature, the reaction mixture was adjusted to pH 8 by adding sodium bicarbonate powder under ice-cooling with stirring. The mixture was diluted with water (200 ml) and extracted with ethyl acetate. The ethyl acetate layer was washed with a saturated aqueous sodium bicarbonate solution, water and brine subsequently, and dried over anhydrous sodium sulfate. The solvent was removed in vacuo, and the residue was purified by column chromatography on aminopropyl silica gel (eluent: ethyl acetate) and recrystallized from diethyl ether/hexane(2/1) to give (R)-3-[7-carbamoyl-5-[2-[[2-(2-ethoxyphenoxy)ethyl] amino]propyl]-1H-indol-1-yl]propyl pivalate (5.21 g) as colorless crystals.

$^1$H-NMR (CDCl$_3$) δ ppm: 1.11 (d, J=6.2 Hz, 3H), 1.21 (s, 9H), 1.27 (t, J=7.0 Hz, 3H), 1.95–2.10 (m, 2H), 2.75 (dd, J=13.6, 6.4 Hz, 1H), 2.85 (dd, J=13.6, 6.6 Hz, 1H), 2.95–3.10 (m, 3H), 3.85–4.00 (m, 4H), 4.00–4.20 (m, 2H), 4.35–4.45 (m, 2H), 5.55–5.65 (br s, 1H), 6.05–6.20 (br s, 1H), 6.47 (d, J=3.2 Hz, 1H), 6.75–6.95 (m, 4H), 7.06 (d, J=3.2 Hz, 1H), 7.21 (d, J=1.5 Hz, 1H), 7.54 (d, J=1.5 Hz, 1H); Specific Rotation: $[α]_D^{27}$=−5.8° (c=1.06, Methanol).

Example 4

The following compound was prepared according to a similar manner to that described in Example 3 using tert-butyl (R)-N-[2-[7-carbamoyl-1-(3-hydroxypropyl)-2,3-dihydro- 1-H-indol-5-yl]-1-methylethyl]-N-[2-[2-(2,2,2-trifluoro-ethoxy)phenoxy]ethyl]carbamate instead of tert-butyl (R)-N-[2-[7-carbamoyl-1-(3-hydroxypropyl)-2,3-dihydro-1H-indol-5-yl]-1-methylethyl]-N-[2-(2-ethoxyphenoxy)-ethyl]carbamate.

(R)-3-[7-Carbamoyl-5-[2-[[2-[2-(2,2,2-trifluoroethoxy)-phenoxy]ethyl]amino]propyl]-1H-indol-1-yl]propyl Pivalate (Compound D)

$^1$H-NMR (CDCl$_3$) δ ppm: 1.11 (d, J=6.2 Hz, 3H), 1.21 (s, 9H) 2.00–2.10 (m, 2H), 2.73 (dd, J=13.5, 6.5 Hz, 1H), 2.84 dd, J=13.5, 6.8 Hz, 1H), 2.95–3.15 (m, 3H), 3.90–4.00 (m, 2H), 4.00–4.30 (m, 4H), 4.35–4.45 (m, 2H), 5.73 (br s, 1H), 6.10 (br s, 1H), 6.47 (d, J=3.2 Hz, 1H), 6.80–7.05 (m, 4H), 7.07 (d, J=3.2 Hz, 1H), 7.19 (d, J=1.4 Hz, 1H), 7.54 (d, J=1.4 Hz, 1H); Specific Rotation: $[α]_D^{27}$=−17.5° (c=0.79, Methanol).

Example 5

(R)-3-[7-Carbamoyl-5-[2-[[2-(2-ethoxyphenoxy) ethyl]amino]-propyl]-1H-indol-1-yl]propyl Pivalate Hydrochloride (Compound C Hydrochloride)

To a solution of (R)-3-[7-carbamoyl-5-[2-[[2-(2-ethoxyphenoxy)ethyl]amino]propyl]-1H-indol-1-yl]propyl pivalate (6.07 g) in ethanol (58 ml) was added dropwise 1N hydrochloric acid (11.6 ml) under ice-cooling with stirring, and the mixture was stirred for 15 minutes under the same condition. The reaction mixture was concentrated in vacua, and to the residue was added ethanol. After azeotropic removal of water, the residue was dissolved in ethanol (6 ml) and ethyl acetate (60 ml) was added to the solution. After the mixture was allowed to stand for 16 hours at room temperature, the resulting colorless crude crystals (5.14 g) were obtained. After the crystals were combined with another crude crystals obtained similarly, recrystallization of the combined crystal (8.12 g) from ethanol/ethyl acetate (15/1) gave (R)-3-[7-carbamoyl-5-[2-[[2-(2-ethoxyphenoxy)ethyl]amino]propyl]-1H-indol-1-yl]propyl pivalate hydrochloride (7.46 g) as colorless crystals.

$^1$H-NMR (CDCl$_3$) δ ppm: 1.21 (s, 9H), 1.29 (t, J=7.0 Hz, 3H), 1.45 (d, J=6.5 Hz, 3H), 1.95–2.10 (m, 2H), 3.12 (dd, J=14.0, 7.2 Hz, 1H), 3.30–3.60 (m, 3H), 3.85–4.05 (m, 5H), 4.30–4.50 (m, 4H) 5.87 (s, 1H), 6.40 (d, J=3.2 Hz, 1H), 6.80–7.00 (m, 4H), 7.05 (d, J=3.2 Hz, 1H), 7.33 (d, J=1.5 Hz, 1H), 7.36 (s, 1H), 7.50 (d, J=1.5 Hz, 1H), 9.10–9.30 (br s, 1H), 9.50–9.65 (br s, 1H); Specific Rotation: $[\alpha]_D^{28}$=–7.0° (c=1.22, Methanol).

Reference Example 5

(R)-3-[7-Carbamoyl-5-[2-[[2-[2-(2,2,2-trifluoroethoxy)-phenoxy]ethyl]amino]propyl]-1H-indol-1-yl]propyl 2-ethyl-butyrate (Compound a)

To a solution of (R)-5-[2-[[2-[2-(2,2,2-trifluoro-ethoxy)phenoxy]ethyl]amino]propyl]-1-(3-hydroxypropyl)- 2,3-dihydro-1H-indole-7-carboxamide (3.0 g) in methylene chloride (50 ml) was added di-tert-butyl dicarbonate (1.32 g) under ice-cooling, and the mixture was stirred for 30 minutes under ice-cooling and overnight at room temperature. The reaction mixture was concentrated in vacuo, and the residue was dissolved in ethyl acetate (50 ml). The solution was washed with 10% aqueous citric acid solution, a saturated aqueous sodium bicarbonate solution and brine subsequently, and dried over anhydrous sodium sulfate. The solvent was removed in vacuo to give pale brown amorphous tert-butyl (R)-N-[2-[7-carbamoyl-1-(3-hydroxypropyl)-2,3-dihydro-1H-indol-5-yl]-1-methylethyl]-N-[2-[2-(2,2,2-trifluoroethoxy)phenoxy]-ethyl]carbamate (2.99 g).

$^1$H-NMR (CDCl$_3$) δ ppm: 1.20–1.50 (m, 12H), 1.70–1.85 (m, 2H) 2.50–4.50 (m, 18H), 5.89 (br s, 1H), 6.69 (br s, 1H), 6.80–7.20 (m, 6H); Specific Rotation: $[\alpha]_D^{25}$=–41.6° (c=1.12, Methanol).

tert-Butyl (R)-N-[2-[7-carbamoyl-1-(3-hydroxy-propyl)-2,3-dihydro-1H-indol-5-yl]-1-methylethyl]-N-[2-[2-(2,2,2-trifluoroethoxy)phenoxy]ethyl]carbamate (12.0 g) and ammonium formate (12.7 g) were dissolved in methanol (300 ml), and 10% palladium on carbon (1.20 g) was carefully added to the solution. The mixture was heated overnight under reflux, and the solvent was removed in vacuo. Water was added to the residue, and the mixture was extracted with ethyl acetate. The ethyl acetate layer was washed with brine, and dried over anhydrous sodium sulfate. The solvent was removed in vacuo to give amorphous tert-butyl (R)-N-[2-[7-carbamoyl-1-(3-hydroxy-propyl)-1H-indol-5-yl]-1-methylethyl]-N-[2-[2-(2,2,2-trifluoroethoxy)phenoxy]ethyl]carbamate (12.2 g).

$^1$H-NMR (CDCl$_3$) δ ppm: 1.1–1.4 (m, 12H), 1.95–2.1 (m, 2H), 2.7–3.0 (m, 2H), 3.25–3.7 (m, 4H), 3.8–4.2 (m, 3H), 4.3–4.6 (m, 4H), 5.91 (br s, 1H), 6.45–6.6 (m, 2H), 6.75–7.6 (m, 7H); Specific Rotation: $[\alpha]_D^{27}$=–44.5° (c=1.11, Methanol).

tert-Butyl (R)-N-[2-[7-carbamoyl-1-(3-hydroxy-propyl)-1H-indol-5-yl]-1-methylethyl]-N-[2-[2-(2,2,2-trifluoroethoxy)phenoxy]ethyl]carbamate (2.00 g) was dissolved in dry pyridine (3 ml), and 2-ethylbutyryl chloride (0.54 g) prepared from 2-ethylbutyric acid and oxalyl chloride was added to the solution. After the mixture was stirred overnight at room temperature, a saturated aqueous sodium bicarbonate solution was added to the reaction mixture, and the mixture was extracted with ethyl acetate. The ethyl acetate layer was washed with a saturated aqueous sodium bicarbonate solution and brine subsequently, and dried over anhydrous magnesium sulfate. The solvent was removed in vacuo, and the residue was purified by column chromatography on silica gel (eluent:hexane/ethyl acetate=2/1) to give white amorphous (R)-3-[5-[2-[N-(tert-butoxycarbonyl)-N-[2-[2-(2,2,2-trifluoroethoxy)phenoxy]ethyl]amino]propyl]-7-carbamoyl-1H-indol-1-yl]propyl 2-ethylbutyrate (1.66 g).

$^1$H-NMR (CDCl$_3$) δ ppm: 0.90 (t, J=7.4 Hz, 6H), 1.10–1.40 (m, 12H) 1.45–1.70 (m, 4H), 1.90–2.10 (m, 2H), 2.15–2.30 (m, 1H), 2.70–3.00 (m, 2H), 3.30–3.70 (m, 2H), 3.80–4.70 (m, 7H), 4.36 (q, J=8.4 Hz, 2H), 5.62 (br s, 1H), 6.40–6.50 (m, 2H), 6.85–7.40 (m, 6H), 7.45–7.55 (m, 1H); Specific Rotation: $[\alpha]_D^{31}$=–41.8° (c=0.99, Methanol).

(R)-3-[5-[2-[N-(tert-Butoxycarbonyl)-N-[2-[2-(2,2,2-trifluoroethoxy)phenoxy]ethyl]amino]propyl]-7-carbamoyl-1H-indol-1-yl]propyl 2-ethylbutyrate (1.56 g) was dissolved in isopropano (10 ml), and concentrated hydrochloric acid (5.0 ml) was added dropwise to the solution under ice-cooling with stirring. After the mixture was stirred for 4 hours at room temperature, a saturated aqueous sodium bicarbonate solution was added to the reaction mixture under ice-cooling, and the mixture was extracted with ethyl acetate. The ethyl acetate layer was washed with brine and dried over anhydrous magnesium sulfate. The solvent was removed in vacuo, and the residue was purified by column chromatography on silica gel (eluent:methylene chloride/methanol=20/1) and recrystallized from diethyl ether-hexane to give (R)-3-[7-carbamoyl-5-[2-[[2-[2-(2,2,2-trifluoroethoxy)phenoxy]ethyl]amino]propyl]-1H-indol-1-yl]propyl 2-ethylbutyrate (1.10 g) as white crystals.

$^1$H-NMR (CDCl$_3$) δ ppm: 0.90 (t, J=7.4 Hz, 6H), 1.11 (d, J=6.2 Hz, 3H), 1.45–1.70 (m, 4H), 2.00–2.10 (m, 2H), 2.15–2.25 (m, 1H), 2.65–2.90 (m, 2H), 2.95–3.15 (m, 3H), 3.99 (t, J=6.3 Hz, 2H), 4.00–4.30 (m, 4H), 4.41 (t, J=6.9 Hz, 2H), 5.64 (br s, 1H), 6.07 (br s, 1H), 6.47 (d, J=3.2 Hz, 1H), 6.80–7.05 (m, 4H), 7.08 (d, J=3.2 Hz, 1H), 7.19 (d, J=1.6 Hz, 1H), 7.54 (d, J=11.6 Hz, 1H); Specific Rotation: $[\alpha]_D^{30}$=–16.4° (c=1.00, Methanol).

Reference Example 6

The following compounds were prepared according to a similar manner to that described in Reference Example 5 using the corresponding acid halide instead of 2-ethylbutyryl chloride.

(R)-3-[7-Carbamoyl-5-[2-[[2-[2-(2,2,2-trifluoroethoxy)-phenoxy]ethyl]amino]propyl]-1H-indol-1-yl]propyl 2,2-dimethylvalerate (Compound b)

$^1$H-NMR (CDCl$_3$) δ ppm: 0.90 (t, J=7.3 Hz, 3H), 1. 11 (d, J=6.2 Hz, 3H), 1.18 (s, 9H), 1.19–1.28 (m, 2H), 1.49–1.53 (mn, 2H), 2.03–2.06 (m, 2H), 2.73 (dd, J=13.5, 6.5 Hz, 1H), 2.84 (dd, J=13.5, 6.8 Hz, 1H), 3.00–3.10 (m, 3H), 3.96 (t, J=6.2 Hz, 2H), 4.07–4.23 (m, 4H), 4.40 (t, J=6.9 Hz, 2H), 5. 66 (br s, 1H), 6.09 (br s, 1H), 6.47 (d, J=3.2 Hz, 1H), 6. 84–7.03 (m, 4H), 7.07 (d, J=3.2 Hz, 1H), 7.19 (d, J=1.6 Hz,

(R)-3-[7-Carbamoyl-5-[2-[[2-[2-(2,2,2-trifluoroethoxy)-phenoxy]ethyl]amino]propyl]1H-indol-1-yl]propyl α,α-dimethylphenylacetate (Compound c)

$^1$H-NMR (CDCl$_3$) δ ppm: 1.10 (d, J=6.2 Hz, 31H), 1.60 (s, 6H) 1.80–1.96 (m, 2H), 2.71 (dd, J=13.7, 6.4 Hz, 1H), 2.82 (dd, J=13.5, 6.7 Hz, 1H), 2.96–3.10 (m, 3H), 3.90 (t, 2H), 4.03–4.28 (m, 6H), 5.58 (br s, 1H), 6.00 (br s, 1H), 6.37 (d, J=3.1 Hz, 1H), 6.84–7.03 (m, 4H), 6.68 (d, J=3.2 Hz, 1H), 7.19 (d, J=1.6 Hz, 1H), 7.54 (d, J=1.6 Hz, 1H); Specific Rotation: $[α]_D^{29}$=−13.7° (c=1.15, Methanol).

(R)-3-[7-Carbamoyl-5-[2-[[2-[2-(2,2,2-trifluoroethoxy)-phenoxy]ethyl]amino]propyl]-1H-indol-1-yl]propyl 2,2-Dimethylbutyrate (Compound d)

$^1$H-NMR (CDCl$_3$) δ ppm: 0.85 (t, J=7.5 Hz, 3H), 1.12 (d, J=6.2 Hz, 3H), 1.17 (s, 6H), 1.57 (q, J=7.5 Hz, 4H), 2.00–2.10 (m, 2H), 2.70–2.90 (m, 2H), 2.95–3.15 (m, 3H), 3.97 (t, J=6.2 Hz, 2H), 4.00–4.40 (m, 4H), 4.40 (t, J=7.0 Hz, 2H), 5.70 (br s, 1H), 6.12 (br s, 1H), 6.47 (d, J=3.2 Hz, 1H), 6.80–7.05 (m, 4H), 7.07 (d, J=3.2 Hz, 1H), 7.19 (d, J=1.6 Hz, 1H), 7.54 (d, J=1.5 Hz, 1H); Specific Rotation: $[α]_D^{31}$=−15.4° (c=1.00, Methanol).

Test Example 1

Test for Measuring α$_1$-adrenoceptor Blocking Effect

Ductus deferenses (about 1.5 cm from testis side) were isolated frommaleWistar rats (about 300 to 350 g in body weight). After removal of the blood vessel and connective tissue, each preparation was vertically suspended in Magnus bath containing 10 ml of Krebs-Henseleit solution maintained at 37° C. and gassed a mixture of 95% oxygen and 5% carbon dioxide under a resting tension of 1 g. A solution of a mixture containing propranorol and yohimbine (final concentration: propranorol 1 μM and yohimbine 0.1 μM) was added into the Magnus bath. After 30 minutes, norepinephrine at the final concentration of 10 μM was added into the Magnus bath until the maximum contraction was obtained, and each preparation was washed. This procedure was repeated several times until the heights of contraction were stable. Each preparation was pre-treated with a solution containing the test compound before 30 minutes, and the contractile responses by treatment of 10 μM norepinephrine were measured. Contraction of each preparation without pre-treatment of the test compound was expressed as 100%. The α$_1$-adrenoceptor blocking effect of the test compound was evaluated as the molar concentration of the compound required producing 50% inhibition of the contraction before the addition of norepinephrine (i.e., IC$_{50}$ value). The results were shown in Table 1.

TABLE 1

| Test compound | IC$_{50}$ (nM) |
| --- | --- |
| Compound A | 2.7 |
| Compound B hydrochloride | 4.3 |
| Bunazosin hydrochloride | 315 |

Test Example 2

Test for Measuring Drug Concentration in Aqueous Humor (1) Method

After 0.1% solution of (R)-5-[2-[[2-(2-ethoxy-phenoxy) ethyl]amino]propyl]-1-(3-hydroxypropyl)-1H-indole-7-carboxamide hydrochloride (Compound B hydrochloride) (50 μl) was instillated on eye of Japanese White rabbits (about 3 kg in body weight; Japan SLC), aqueous humor was collected with the time course. To the collected aqueous humor (0.1 ml) was added (R)-3-chloro-1-(3-hydroxypropyl)-5-[2-[[2-[2-(2,2,2-trifluoroethoxy) phenoxy]ethyl]amino]propyl]-1H-indole-7-carboxamide (10 ng) as an internal standard, and 0.1M phosphate buffer (pH7.6) and sodium chloride (about 1 g) were added to the mixture. The resulting mixture was extracted with diethyl ether (5 ml), and the diethyl ether layer was concentrated under a stream of nitrogen. After the residue was dissolved in mobile phase (200 μl), 100 μl of the solution was injected into high performance liquid chromatography and the Compound B was determined in the following conditions. The results were shown in Table 2.

(2) HPLC Conditions

Analytical column: Inertsil ODS-3 (4.6×250 mm)

Mobile phase: acetonitrile/0.1% phosphoric acid+2 mM sodium laurylsulfate=1/1

Column temperature: 50° C.

Flow rate: 1.0 ml/minute

Fluorometry: excitation wave length 270 nm, emission wave length 435 nm

TABLE 2

| | Drug concentrations (ng/ml) | | |
| --- | --- | --- | --- |
| Test compound | 20 minutes after | 2 hours after | 6 hours after |
| Compound B | 2 | 20 | 8 |

Test Example 3

Test for Rate of Hydrolysis by Endogenous Enzyme (3) Method

To whole blood (0.5 ml) collected from male Wistar rats as heparinized blood were respectively added each ester derivative (1 μg) of (R)-1-(3-hydroxypropyl)-5-[2-[[2-[2-(2,2,2-trifluoroethoxy)phenoxy]ethyl]amino]propyl]-1H-indole-7-carboxamide (Compound A) and internal standard [(R)-3-chloro-1-(3-hydroxypropyl)-5-[2-[[2-[2-(2,2,2-trifluoroethoxy)phenoxy]ethyl]amino]propyl]-1H-indole-7-carboxamide] (1 μg), and the mixture was incubated at 37° C. After 15 minutes, 30 minutes, 1 hour and 2 hours, 0.7M aqueous sodium fluoride solution (0.5 ml) as an esterase inhibitor was added to each sample to stop the reaction. 0.1 M Phosphate buffer (pH7.6) and sodium chloride (about 1 g) were added to the mixture, the resulting mixture was extracted with diethyl ether (5 ml), and the diethyl ether layer was concentrated under a stream of nitrogen. After the residue was dissolved in mobile phase (300 μl), 10 μl of the solution was injected into high performance liquid chromatography, and the test compound and Compound A were determined in the following conditions. The results were shown in Table 3.

(2)HPLC Conditions
Analytical column: Inertsil ODS-3 (4.6×250 mm)
Mobile phase: acetonitrile/20 mM acetate buffer (pH 5.0)=40/60 Column temperature: 50° C.
Flow rate: 1.0 ml/minute
Fluorometry: excitation wavelength 270 nm, emission wavelength 435 nm

TABLE 3

| Test compound | Decomposition rate (%) | | | |
| --- | --- | --- | --- | --- |
| | 15 minutes after | 30 minutes after | 1 hour after | 2 hours after |
| Compound D | 54.8 | 67.1 | 86.5 | 98.6 |
| Compound a | 8.4 | 12.0 | 12.6 | 25.2 |
| Compound b | 2.2 | 3.8 | 7.5 | 10.2 |
| Compound c | 0.6 | 1.6 | 3.2 | 3.7 |
| Compound d | 2.1 | 5.6 | 8.4 | 21.7 |

Test Example 4

Test for Measuring Drug Concentration in Aqueous Humor (2)

(1)Method

After 0.1% solution (50 μl) of (R)-3-[7-carbamoyl-5-[2-[[2-(2-ethoxyphenoxy)ethyl]amino]propyl]-1H-indol-1-yl]propyl pivalate hydrochloride (Compound C hydrochloride) was instilled on eye of Japanese White rabbits (about 3 kg in body weight; Japan SLC), aqueous humor was collected with the time course. To the collected aqueous humor (0.1 ml) was added internal standard [(R)-3-chloro-1-(3-hydroxypropyl)-5-[2-[[2-[2-(2,2,2-trifluoroethoxy)phenoxy]ethyl]amino]propyl]-1H-indole-7-carboxamide] (10 ng), and 0.1M phosphate buffer (pH7.6) and sodium chloride (about 1 g) were added to the mixture. The resulting mixture was extracted with diethyl ether (5 ml), and the diethyl ether layer was concentrated under a stream of nitrogen. After the residue was dissolved in mobile phase (200 μl), 100 μl of the solution was injected into high performance liquid chromatography, and the Compound C and (R)-5-[2-[[2-(2-ethoxyphenoxy)ethyl]amino]propyl]-1-(3-hydroxypropyl)-1H-indole-7-carboxamide (Compound B) was determined in the following conditions. The results were shown in Table 4.

(2)HPLC Conditions

Analytical column: Inertsil ODS-3 (4.6×250 mm)
Mobile phase: acetonitrile/0.1% phosphoric acid+2 mM sodium laurylsulfate=1/1
Column temperature: 50° C.
Flow rate: 1.0 ml/minute
Fluorometry: excitation wave length 270 nm, emission wave length 435 nm

TABLE 4

| Test compound | Drug concentrations (ng/ml) | | |
| --- | --- | --- | --- |
| | 20 minutes after | 2 hours after | 6 hours after |
| Compound B | 140 | 546 | 136 |
| Compound C | <1 | <1 | <1 |

Test Example 5

Stability Test

The test compounds were dissolved in 0.1M acetate buffer (pH 5.0) to prepare 0.1% solutions. Each 0.1% solution was allowed to stand in the dark for 28 days at 40° C., 50° C., 60° C. and 70° C., respectively. The results were shown in Table 5.

TABLE 5

| Test compound | Residual rate (%) | | | |
| --- | --- | --- | --- | --- |
| | 40° C. | 50° C. | 60° C. | 70° C. |
| Compound D | 99.9 | 99.7 | 99.5 | 98.9 |
| Compound A | 0.1 | 0.3 | 0.5 | 1.1 |

Test Example 6

Acute Toxicity Test

Male SD rats of 7 weeks age (n=5; 190–210 g in body weight) were fasted for 18 hours. (R)-3-[7-Carbamoyl-5-[2-[[2-(2-ethoxyphenoxy)ethyl]amino]propyl]-1H-indol-1-yl]propyl pivalate hydrochloride which was suspended in 0.5% aqueous methylcellulose solution at a concentration of 100 mg/ml was orally administered to the rats at a dose of 1000 mg/kg. Any fatal rats were not observed during 24 hours after the administration.

What is claimed is:

1. An indole derivative represented by the general formula:

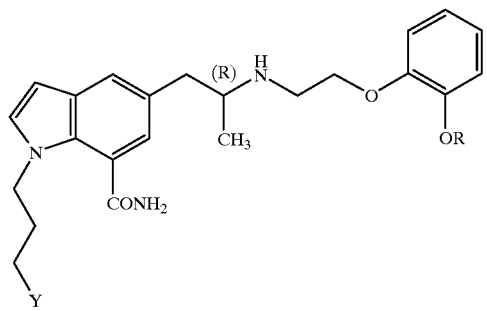

(wherein R represents an ethyl group or a 2,2,2-trifluoroethyl group; Y represents a hydroxy group or a pivaloyloxy group with the proviso that Y represents a pivaloyloxy group when R represents a 2,2,2-trifluoroethyl group; and the carbon atom marked with (R) represents a carbon atom in (R) configuration) or a pharmaceutically acceptable salt thereof.

2. An indole derivative as claimed in claim 1, represented by the general formula:

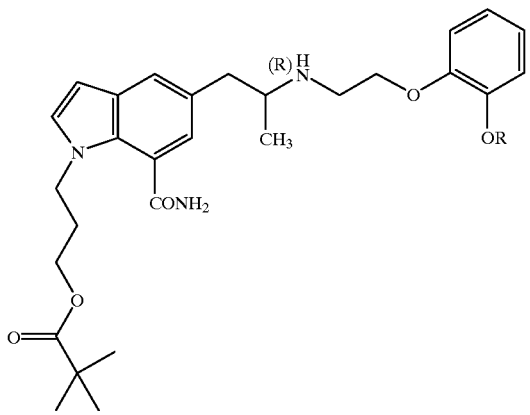

(wherein R represents an ethyl group or a 2,2,2-trifluoroethyl group; and the carbon atom marked with (R) represents a carbon atom in (R) configuration) or a pharmaceutically acceptable salt thereof.

3. The indole derivative as claimed in claim 1, represented by the formula:

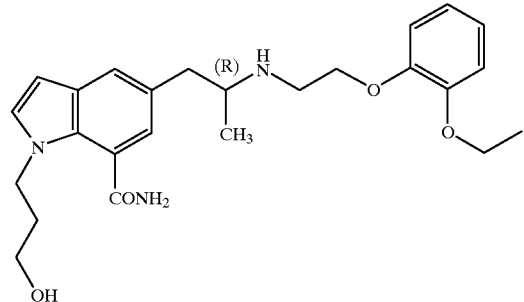

(wherein the carbon atom marked with (R) represents carbon atom in (R) configuration) or a pharmaceutically acceptable salt thereof.

4. A pharmaceutical composition comprising an indole derivative represented by the general formula:

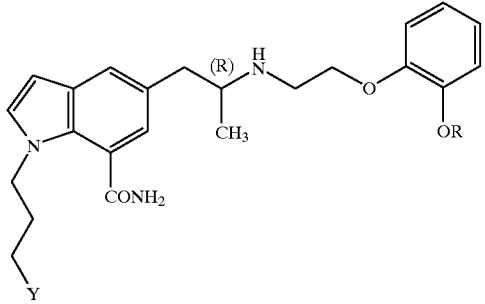

(wherein R represents an ethyl group or a 2,2,2-trifluoroethyl group; Y represents a hydroxy group or a pivaloyloxy group with the proviso that Y represents a pivaloyloxy group when R represents a 2,2,2-trifluoroethyl group; and the carbon atom marked with (R) represents a carbon atom in (R) configuration) or a pharmaceutically acceptable salt thereof.

5. A pharmaceutical composition as claimed in claim 4, comprising an indole derivative represented by the general formula:

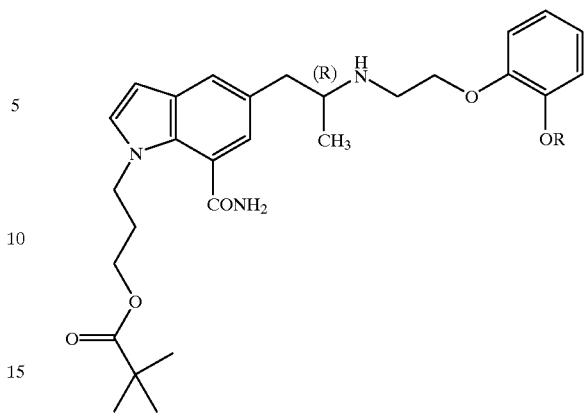

(wherein R represents an ethyl group or a 2,2,2-trifluoroethyl group; and the carbon atom marked with (R) represents a carbon atom in (R) configuration) or a pharmaceutically acceptable salt thereof.

6. A method for the prevention or treatment of glaucoma or ocular hypertension which comprises administering a therapeutically effective amount of an indole derivative represented by the general formula:

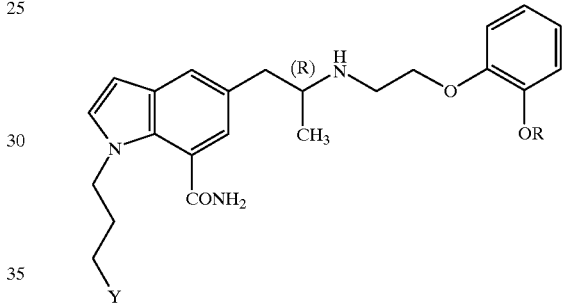

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

7. A method for the prevention or treatment of glaucoma or ocular hypertension as claimed in claim 6, which comprises administering a therapeutically effective amount of an indole derivative represented by the general formula:

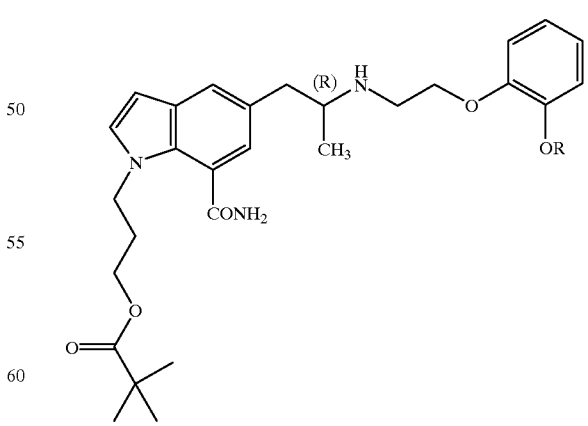

(wherein R represents an ethyl group or a 2,2,2-trifluoroethyl group; and the carbon atom marked with (R) represents a carbon atom in (R) configuration) or a pharmaceutically acceptable salt thereof.

8. A method for lowering intraocular pressure, which comprises administering a therapeutically effective amount of an indole derivative represented by the general formula:

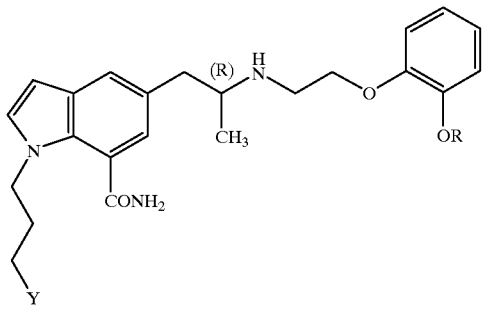

(wherein R represents an ethyl group or a 2,2,2-trifluoroethyl group; Y represents a hydroxy group or a pivaloyloxy group; and the carbon atom marked with (R) represents a carbon atom in (R) configuration) or a pharmaceutically acceptable salt thereof.

9. A method for lowering intraocular pressure as claimed in claim 8, which comprises administering a therapeutically effective amount of indole derivative represented by the general formula:

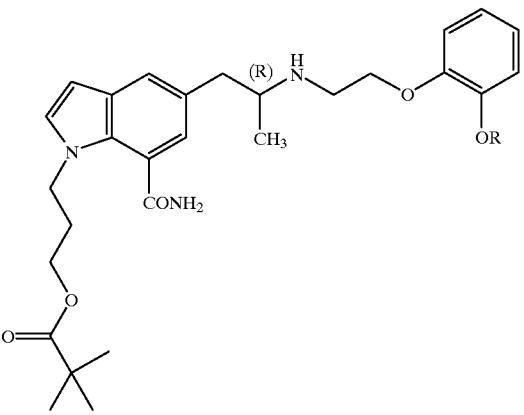

(wherein R represents an ethyl group or a 2,2,2-trifluoroethyl group; and the carbon atom marked with (R) represents a carbon atom in (R) configuration) or a pharmaceutically acceptable salt thereof.

10. The method of claim 7, wherein said indole derivative is administered topically to the eye.

11. The method of claim 7, wherein said indole derivative is administered to the eye in the form of eye drops.

12. The method of claim 9, wherein said indole derivative is administered topically to the eye.

13. The method of claim 9, wherein said indole derivative is administered to the eye in the form of eye drops.

* * * * *